(12) United States Patent
Nakamura et al.

(10) Patent No.: US 8,883,495 B2
(45) Date of Patent: Nov. 11, 2014

(54) HUMAN T-CELL POPULATION (75) Inventors: Shuji Nakamura, Okayama (JP); Ryuichi Motoda, Okayama (JP); Masayoshi Kibata, Okayama (JP); Kunzo Orita, Okayama (JP); Fumiyuki Yamasaki, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 1503 days.

(21) Appl. No.: 12/282,977

(22) PCT Filed: Mar. 15, 2007

(86) PCT No.: PCT/JP2007/055228
§ 371 (c)(1),
(2), (4) Date: Sep. 15, 2008

(87) PCT Pub. No.: WO2007/105797
PCT Pub. Date: Sep. 20, 2007

(65) Prior Publication Data
US 2009/0297490 A1 Dec. 3, 2009

(30) Foreign Application Priority Data
Mar. 15, 2006 (JP) ................. 2006-070372

(51) Int. Cl.
C12N 5/00 (2006.01)
A61K 35/14 (2006.01)
C12N 5/0783 (2010.01)
A61K 35/12 (2006.01)

(52) U.S. Cl.
CPC ......... *C12N 5/0636* (2013.01); *A61K 2035/122* (2013.01); *A61K 35/17* (2013.01)
USPC ........................................ 435/325; 424/93.7

(58) Field of Classification Search
CPC ............. A61K 2300/00; C12N 5/0636; C12N 2501/515; C12N 5/0637; C12N 5/0638; C12N 5/0694
See application file for complete search history.

(56) References Cited

FOREIGN PATENT DOCUMENTS

JP 2005-245430 A 9/2005

OTHER PUBLICATIONS

Tong J.-J. et al. 1999. A bone marrow-derived stroma cell line, ST2, can support the differentiation of fetal thymocytes from the CD4– CD8– double negative to the CD4+ CD8+ double positive differentiation stage in vitro. Immunology 97:672-78.*
Petra Hoffman et al., Large-Scale In Vitro Expansion of Polyclonal Human DC4+CD25high Regulatory T Cells, American Society of Hematology, vol. 104, No. 3, Aug. 1, 2004, pp. 895-903.
S. Sakaguchi, "Naturally Arising CD4+ Regulatory T Cells for Immunologic Self-Tolerance and Negative Control of Immune Responses," Annual Review of Immunology, (2004), vol. 22, pp. 531-562.
J.D. Fontenot et al., "Foxp3 programs the development and function of CD4+CD25+ regulatory T cells," Nature Immunology, (2003), vol. 4, pp. 330-336.
T. Takahashi et al., "Immunologic Self-Tolerance Maintained by CD25+CD4+ Regulatory T Cells Constitutively Expressing Cytotoxic T Lymphocyte-associated Antigen 4," Journal of Experimental Medicine, (2000), vol. 192, pp. 303-309.
L. Cosmi et al., "Human CD8+CD25+ thymocytes share phenotypic and functional features with CD4+CD25+ regulatory thymocytes," (2003) 102:4107-4114.
M-J Xu et al., "Stimulation of Mouse and Human Primitive Hematopoiesis by Murine Embryonic Aorta-Gonad-Mesonephros-Derived Stromal Cell Lines," (1998), vol. 92, No. 6, pp. 2032-2040.
Y. Nakamura et al., "Ex Vivo Generation of CD34+ Cells From CD34– Hematopoietic Cells," (1999), vol. 92, No. 12, pp. 4053-4059.
W.R. Godfrey et al., "Cord blood CD4+CD25+-derived T regulatory cell lines express FOXP3 protein and manifest potent suppressor function," (2005), vol. 105, No. 2, pp. 750-758.
W.J. Grossman et al., "Human T Regulatory Cells Can Use the Perforin Pathway to Cause Autologous Target Cell Death," Immunity 2004, vol. 21, pp. 589-601.
K.J.L. Hammond et al., "NKT cells are phenotypically and functionally diverse," Eur. J. Immunol. (1999), vol. 29, pp. 3768-3781.
S. Nakamura et al., "IL-2-independent generation of FOXP3+CD4+CD8+CD25+ cytotoxic regulatory T cell lines from human umbilical cord blood," Exp. Hematol. (2007), vol. 35, pp. 287-296.
S. Nakamura et al., "Kogan Sayo, Men'Eki Yokusei Sayo O Motsu Ketsueki Saibo 'Hozot'", Bionics, (2007), vol. 4, No. 3, pp. 84-87.
Nakamura et al.,"IL-2-Independent Generation of Novel Cytotoxic Regulatory T Cell Lines (Hozot) From Human Umbilical Cord Blood," Proceedings of the Japanese Society for Immunology (JSI), (2006), vol. 36, pp. 224 (Abstract 3-C-W37-4-P).
Huang, Y. et al., "Ex vivo Expansion of V-alpha24 Natural Killer T Cells with alpha-galactosylceramide," Acta Academiae Medicinae Sinicae (2005), vol. 27, pp. 315-320.
Inoue et al., "Xenogenic Cytotoxic Activity of Novel Regulatory T Cell Lines (Hozot)," Japanese Society for Immunology, 2006, vol. 36, p. 225 (Abstract 3-C-W37-5-P).
Tsuji-Takayama et al., "IL-2 Selectively Enhanced IL-10 Production From Novel Cytotoxic Regulatory T Cell Lines (Hozot)," Japanese Society for Immunology, 2006, vol. 36, p. 225 (Abstract 3-C-W37-6-P).
Suzuki et al.,"Suppressive Activity Mechanisms of Novel Cytotoxic Regulatory T Cell Lines (Hozot)," Japanese Society for Immunology, 2006, vol. 36, p. 225 (Abstract 3-C-W37-7-P).

* cited by examiner

*Primary Examiner* — Lora E Barnhart Driscoll
(74) *Attorney, Agent, or Firm* — Browdy and Neimark, PLLC (57) ABSTRACT

The present invention has objects to provide a novel human T-cell population having both cytotoxic and immunosuppressive activities, and to a method for preparing the same. The above objects are attained by providing a human T-cell population which is obtainable by coculturing mononuclear cells, collected from human blood, with stroma cells and which has the following features:

(1) being positive for CD3, CD25, CD28 and T-cell antigen receptor αβ;
(2) essentially consisting of three groups of a CD4 positive and CD8 positive ($CD4^+CD8^+$) T-cell group, a CD4 positive and CD8 dimly positive ($CD4^+CD8^{dim}$) T-cell group, and a CD4 negative and CD8 positive ($CD4^-CD8^+$) T-cell group;
(3) exerting a cytotoxic activity against the cocultured stroma cells; and
(4) exerting an immunosuppressive activity against activated T cells.

3 Claims, 3 Drawing Sheets

HUMAN T-CELL POPULATION

TECHNICAL FIELD

The present invention relates to a novel human T-cell population, particularly, to a novel human T-cell population which is obtainable through a coculturing with stromal cells and which has a cytotoxic activity and immunosuppressive activity.

BACKGROUND ART

T cells are one of the cell populations playing major roles in the immune system as a biodefence system against various pathogens. Such T cells are roughly classified into CD4 positive helper T cells and CD8 positive cytotoxic T cells, where the former relates to the promotion of immune response and the latter relates to the exclusion of virus-infected cells and tumor cells. Helper T cells are further classified into Type I helper T cells for promoting cellular immunity and Type II helper T cells for promoting humoral immunity. These T cells with such diversified properties have a function of excluding pathogens and gaining infection resistance under a well-balanced immune response.

In general, under the normal immune response, the exclusion mechanism could not be workable because of the established immunological tolerance against autoantigens as constituents of living bodies. Self-reactive T cells induce both cell death and non-responsiveness against autoantigens. Particularly, it is said that regulatory T cells positively participate in such inhibitory action. Regulatory T cells are defined based on their inhibitory action against other T cells and recently they have been researched as a cell population with a function of inhibiting a specific immunological response and there have been reported diversified regulatory T cells which differ each other in their cell surface markers, types of cytokines produced, and immune inhibitory mechanisms.

Among such regulatory T cells, most well researched are CD4$^+$CD25 regulatory T cells (CD4$^+$CD25$^+$T$_{reg}$) disclosed by S. Sakaguchi, "*Naturally arising CD4 regulatory T cells for immunologic Self-tolerance and negative control of immune responses*", Annual Review of Immunology, Vol. 22, pp. 531-562, 2004. In conventional research results reported so far, the above-identified cells are positive for CD4 and CD25, speculating that CD4 and CD25 can be markers for regulatory T cells. CD4$^+$CD25$^+$T$_{reg}$ are reported to express FORKHEAD BOX P3 (FOXP3) by J. D. Fontenot, M. A. Gavin, and A Y. Rudensky, "*Foxp3 programs the development and function of CD4$^+$CD25 regulatory T cells*", Nature Immunology, Vol. 4, No. 4, pp. 330-336, 2003, and to express T lymphocyte-associated antigen 4 (CTLA-4) that leads T cells to unresponsiveness by T. Takahashi, T. Tagami, S. Yamazaki, T. Ueda, J. Shimizu, N. Sakaguchi, Tak. W. Mak, and S. Sakaguchi, "*Immunologic Self-Tolerance Maintained by CD25$^+$CD4$^+$ Regulatory T cells Constitutively Expressing Cytotoxic T Lymphocyte-associated Antigen 4*", Journal of Experimental Medicine, Vol. 192, pp. 303-309, 2000. T Cells with CD8$^+$CD25$^+$ markers and immunosuppressive activity are disclosed by L. Cosmi, F. Liotta, E. Lazzeri, M. Francalanci, R. Angeli, B. Mazzinghi, V. Santarlasci, R. Manetti, V. Vanini, P. Romagnani, E. Maggi, S. Romagnani, and F. Annunziato, "*Human CD4$^+$CD25$^+$ thymocytes share phenotypic and functional features with CD4$^+$CD25 regulatory thymocytes*", Blood, Vol. 102, No. 12, pp. 4107-4114, 2003.

As for T cells with a cytotoxic activity, CD8$^+$ cytotoxic T cells are well known as described above and they express a cytotoxic activity with a relatively high specificity against target cells. Japanese Patent Kokai No. 2005-245430 discloses a coculture of such T cells with either a tumor cell or a protein specific to the tumor cell to exert a cytotoxic activity specific to the cell.

At present, transplantation of hematopoietic stem cells has been actually realized and there has been desired an appropriate ex vivo cell culture technique for obtaining a sufficient amount of hematopoietic stem cells. In culturing hematopoietic stem cells, a quasi-in vivo environmental coculture with stroma cells is requisite, however, there has not yet been found any human stroma cell line that can be cultured for a relatively long period of time and that sufficiently supports hematopoietic cells, and also there has been pointed out as a problem that human stroma cells secrete a cytokine capable of partially differentiating hematopoietic stem cells. A method for culturing hematopoietic stem cells, derived from human cord blood, using a non-human heterogenic stroma cell line, has been researched; trials of proliferation cultures for either coculturing with mouse stroma cells CD34$^+$ cell derived from human cord blood disclosed by Ming-jiang Xu, K. Tsuji, T. Ueda, Y. Mukouyama, T. Hara, Feng-Chun Yang, Y. Ebihara, S. Matsuoka, A. Manabe, A. Kikuchi, M. Ito, and A. Miyajima, "*Stimulation of Mouse and Human Primitive Hematopoiesis by Murine Embryonic Aorta-Gonad-Mesonephros-Derived Stromal Cell Lines*", Blood, Vol. 92, No. 6, pp. 2032-2040, 1998; or coculturing with mouse stroma cells CD34$^-$cell derived from human cord blood disclosed by Y. Nakamura, K. Ando, J. Chargui, H. Kawada, T. Sato, T. Tsuji, T. Hotta, and S. Kato, "*Ex Vivo Generation of CD34$^+$ Cells From CD34$^-$ Hematopoietic Cells*", Blood, Vol. 94, No. 12, pp. 4053-4059, 1999. Cell populations cultured by the above cocultures are deemed to have no such activities because the cocultures, however, aim to proliferate a hematopoietic cell population excluding proliferated cell population and because immunosuppressive and cytotoxic activities are of proliferated hematopoietic cells.

Although T cells play an important role in the immune system, they have not yet been used as pharmaceuticals because of their unknown aspects still remained. Establishment of a novel human T-cell population has been in a great demand for use in researches and pharmaceuticals.

DISCLOSURE OF INVENTION

Under these circumstances, the present invention has objects to provide a novel human cell population and a method of obtaining the same.

The present inventors energetically researched and found that a human T-cell population which proliferates while imparting a cytotoxic activity to stroma cells by coculturing in vivo mononuclear cells isolated from blood with stroma cells. They also found that the human T-cell population exerts a cytotoxic activity against not only stroma cells used for obtaining the human T-cell population but also another stroma cells other than the human T-cell population and some kinds of tumor cell lines, and exerts an immunosuppressive activity against activated human T cells; most of the cells in the human T-cell population are positive for cell membrane antigens such as CD3, CD25, CD28, and T-cell antigen receptor αβ (TCRαβ); and the human T-cell population could not directly be obtained from living bodies, in which coexist three groups of a CD4$^+$CD8$^+$ group, a CD4$^+$CD8$^{dim}$ group, and a CD4$^-$CD8$^+$ group. Thus, the present inventors confirmed that the human T-cell population is novel, and they accomplished this invention.

The present invention attains the above objects by providing a novel human T-cell population having both cytotoxic and immunosuppressive activities, and a method of obtaining the same.

According to the present invention, a desired T-cell population having both cytotoxic and immunosuppressive activities is obtained. The human T-cell population is a novel one which is not directly obtainable from living bodies and is useful for researches. Pharmaceutical compositions containing the same are useful for treating cancerous-, autoimmune-, and allergic-diseases; and for relieving rejection reaction during transplantation and graft-versus-host reaction.

EXPLANATION OF SYMBOLS

1: $CD4^+CD25^+$ Regulatory T cells
2: $CD4^+CD25^+$ Regulatory T cells treated with anti-CD3/CD28 antibody
3: Human T-cell population U3
4: Human T-cell population U3
5: Group A in Human T-cell population U3
6: Group B in Human T-cell population U3
7: Group C in Human T-cell population U3

BEST MODE FOR CARRYING OUT THE INVENTION

The human T-cell population of the present invention, which is obtainable by coculturing mononuclear cells collected from human blood with stroma cells, has the following features:
(1) being positive for CD3, CD25, CD28 and TCRαβ;
(2) essentially consisting of a CD4 positive and CD8 positive ($CD4^+CD8^+$) group, a CD4 positive and CD8 dimly positive ($CD4^+CD8^{dim}$) group, and a CD4 negative and CD8 positive ($CD4^-CD8^+$) group;
(3) exerting a cytotoxic activity against the stroma cells used in coculture; and
(4) exerting an immunosuppressive activity against activated T cells.

In addition to the above features, the human T-cell population of the present invention produces interleukin 10 (IL-10) in the presence of interleukin 2 (IL-2).

The human T-cell population of the present invention is obtainable by coculturing mononuclear cells isolated from human blood with stroma cells. Any of human blood can be used in the present invention; cord blood, peripheral blood, and bone marrow fluid can be used, and among which cord blood and peripheral blood can be advantageously used because they are easily obtainable in a desired amount from the same donor. The cord blood has been easily collected under informed consent as the recent prevailing technique for cord blood transplantation. To obtain the human T-cell population of the present invention, it does not require a $CD34^+$ cell population as the main object for collecting cord blood now practicing in the art, and even the remaining mononuclear cells separated from $CD34^+$ cells can be used. The fact that there exists no such a $CD34^+$ cell population in the human T-cell population of the present invention would indicate that such population will be disappeared during preparation of the human T-cell population. While, as the merit, peripheral blood can be repeatedly collected from the same donor and it can be applied to a therapy or an ex vivo therapy comprising the steps of applying the method for obtaining the human T-cell population of the present invention to peripheral blood collected from a patient and to collect the desired human T-cell population of the present invention, and restoring it to the same patient. Although the human T-cell population would possibly be collected from any blood samples, the desired human T-cell population could not be obtained depending on donors or it could not necessarily be collected from specific donors, even if the human T-cell population was once successfully collected from such donors.

Examples of the method for collecting mononuclear cells from human blood include density-gradient centrifugation using conventional FICOLL-HYPAQUE or the like. The isolated mononuclear cells are cultured by conventional methods in media used for blood cells, such as D-MEM medium, α-MEM medium, and RPMI 1640 medium. Media supplemented with fetal calf serum at an appropriate concentration can be optionally used. To obtain the human T-cell population of the present invention, important is a step for coculturing mononuclear cells, collected from blood, with stroma cells and it could not be obtained by a single culture of mononuclear cells or by a coculture of mononuclear cells with another cells other than stroma cells. Stroma cells are said to be essential cells in culturing systems for hematopoietic stem cells, and they have an ability of proliferating hematopoietic stem cells through cell adhesion and via the action of chemokines. Examples of the stroma cells usable in the present invention include commercialized mouse stroma cell lines, for example, ST2 cells, OP9 cells, and MC3T3-G2/PA6 cells in terms of their availability; and normal stroma cells collected from mice can be used, if necessary. Mammalian stroma cells other than mice stroma cells, such as human stroma cells, can be used. Prior to use, stroma cells are inoculated to microplates along with an appropriate culture medium, and cultured for one to several days until they proliferate up to confluent state over the bottom surface of each well. To the proliferated stroma cells are added mononuclear cells in an amount of 0.2 to 10 times, preferably, 1 to 4 times by the cell number, and the resulting cells are cultured at 37° C. in 5% $CO_2$ atmospheric conditions, resulting in a gradual reduction of viable stroma cells. This phenomenon can be estimated that the mononuclear cells are stimulated by cell adhesion with the stroma cells to promote their cell differentiation and to generate a cell population with a cytotoxic activity, resulting in disrupting the stroma cells. Since the complete disruption of stroma cells inhibits the proliferation of mononuclear cells, the resulting culture medium containing mononuclear cells should be transferred to a fresh microplate to which stroma cells have been adhered. In transferring, after the initiation of increasing the number of mononuclear cells, the suspended cells are successively collected with a pipet or the like at an interval of one to several days, and the collected cells are transferred to another fresh microplate to which stroma cells have been adhered. To the original microplate is added a freshly prepared medium, followed by continuously culturing the cells until the suspended cells are collected. When these procedures are continued until the stroma cells in the original microplate completely die, the desired mononuclear cells can be efficiently collected. A three to eight weeks of continuous cell culture like this will generate a cell population with cells differentiated up to T cells.

In preparing the human T-cell population of the present invention, to inhibit the proliferation of IL-2 dependent activated T cells coexisting in mononuclear cells collected from blood, such mononuclear cells are usually cultured in the absence of cytokine, particularly, in the absence of IL-2 for three to eight weeks. In the case that a culture medium may possibly contain IL-2, it can be arbitrarily assayed for IL-2 level by, for example, a commercialized EIA kit using an anti-IL-2 antibody. When IL-2 is detected, it can be suitably neutralized by adding an anti-IL-2 antibody to the culture medium.

The human T-cell population of the present invention thus obtained could not be maintained for only one week at longest under a single cell culture condition, however, it can be maintained for about one month when continued coculturing with stroma cells. Even though the human T-cell population will die after gradual reduction of its proliferation activity, it can be continued culturing for about two months when cultured in the presence of a cytokine such as IL-2 or interleukin-15 (IL-15). The human T-cell population can be proliferated by the action of any of the above cytokines, however, the properties (cytotoxic activity, immunosuppressive activity, and cell membrane antigens) may be changed to some extent and therefore the human T-cell population would be used, usually, within one month, preferably, within two weeks after initiating the proliferation culture with the above cytokine(s). Particularly, the human T-cell population prepared from peripheral blood may contain T cells with $CD4^{dim}CD8^{dim}TCR\gamma\delta^+$, which are not found in those prepared from cord blood and the percentage of which may increase when subjected to proliferation culture in the presence of IL-2.

Since almost all the cells in the human T-cell population of the present invention are positive for cell membrane antigens specific to T cells, such as CD3, CD25, CD28 and $TCR\alpha\beta$, the human T-cell population would be a substantially complete T cell population. Also the human T-cell population would be a normal T-cell population because it could not be obtained without coculturing with stroma cells and it is free of virus infection, as well as exhibiting a cytospin image in the form of a normal lymphocyte and showing no abnormal chromosomal karyotype.

The human T-cell population consists essentially of Group A with $CD4^+CD8^+$, Group B with $CD4^+CD8^{dim}$, and Group C with $CD4^-CD8^+$, and the total percentage of these three groups reaches 90% or over, preferably, 93% or over to the total cells in the human T cell population. The percentages of the three groups are determined by flow cytometry using an anti-CD4 antibody and anti-CD8 antibody in combination: Group A ranges from 7.9 to 51.6%; Group B, 1.1 to 71.7%; and Group C, 11.8 to 79.4%. The percentage of Group B tends to lower but that of Group C tends to increase as the increase of culturing time. Separatory collection of these groups can be optionally conducted by conventional cell sorting method using an anti-CD4 antibody and anti-CD8 antibody.

The human T-cell population exhibits a cytotoxic activity against stroma cells used in coculturing for its preparation. The cytotoxic activity is measured by the method in the later described Example 4. Almost most of the stroma cells used for preparing the human T-cell population of the present invention will die when the ratio of the human T-cell population as effector cells (E) to stroma cells as target cells (T) (E/T ratio) is 1/1 or higher. In the case of using cells of a mouse stroma cell line as stroma cells, the human T-cell population exerts a cytotoxic activity against cells of another stroma cell line different from those of the mouse stroma cell line used to prepare the human T cell population. The human T-cell population may exert a cytotoxic activity against cells of mouse or human tumor cell lines. As described in the later described Examples, three groups of human T cell population, which have been separatory collected by cell sorting method using an anti-CD4 antibody and anti-CD8 antibody, exert a cytotoxic activity against ST2 cells as a mouse stroma cell line, used to prepare the human T cell population. Since cytotoxic T cells are usually CD8 positive, Group C with $CD4^-CD8^+$ of the human T-cell population may correspond to such cytotoxic T cells. While, Group A with $CD4^+CD8^+$ and Group B with $CD4^+CD8^{dim}$ in the human T-cell population of the present invention do not correspond to $CD8^+$ cytotoxic T cells and therefore they would possibly be novel T cell populations.

The human T-cell population of the present invention exerts an immunosuppressive activity against activated human T cells. The immunosuppressive activity can be determined by, for example, autologous mixed-lymphocyte reaction used for assaying immunoregulatory activity of $CD4^+CD25^+T_{reg}$, disclosed in the latter mentioned Example 8. With this assay, a relatively high immunosuppressive activity is detected in the human T-cell population and Groups A and C contained therein, indicating that the human T-cell population has a similar immunosuppressive activity as of $CD4^+CD25^+T_{reg}$. While an occasionally generated group (Group D) with CD4 CD8 in the above human T-cell population collected from peripheral blood, which has, as characteristic features, a relatively high cytotoxic activity and a relatively low immunosuppressive activity compared with other groups and exhibits a phenotype of $TCR\gamma\delta^+$, indicating that Group D would be conventionally known cytotoxic T cells. Group D can be separated or removed by magnetic separation using an anti-$TCR\gamma\delta$ antibody.

As disclosed in the later mentioned Example 9, the human T-cell population expresses FOXP3, a transcription factor, as a characteristic feature of $CD4^+CD25^+T_{reg}$, in a rather low expression level. The human T-cell population neither proliferates even when treated with anti-CD3/CD28 antibody nor substantially increases in its FOXP3 expression level. According to literatures, treatment with anti-CD3/CD28 antibody is essential to obtain $CD4^+CD25^+T_{reg}$. Since there needs no step for treatment with CD3/CD28 antibody in the steps for preparing the human T-cell population of the present invention, it is concluded that conventionally known $CD4^+CD25^+T_{reg}$ have not proliferated in the steps or died and they are not contained in the human T cell population.

All three groups, which had been separatory collected by cell sorting method, expressed FOXP3, while FOXP3 was slightly expressed even in Group A with $CD4^+CD8^+$ and Group C with $CD4^+CD8^+$, as well as in Group B with $CD4^+CD8^{dim}$ which might possibly contain the above $CD4^+CD25^{30}T_{reg}$. This leads to a conclusion that the human T-cell population of the present invention does possibly contain a particular regulatory T cell different from conventional $CD4^+CD25^+T_{reg}$.

As described in the later described Examples, the human T-cell population produces interleukin 10 (IL-10). Usually, IL-10 is produced by helper T cells, type II; or regulatory T cells, and it is known that IL-10 inhibits the activity of helper T cells, type I, and those of macrophages. Accordingly, part of the immunosuppressive activity of the human T-cell population of the present invention would be exerted through the action of IL-10.

As described above, the human T-cell population of the present invention is a human T-cell population which has both cytotoxic and immunosuppressive activities. $CD4^+CD8^+$ T cells have been recognized as a juvenile T-cell population and there has not yet been known any population with the above-identified activities. Therefore, at least Group A with $CD4^+CD8^+$ is a novel human T cell population. Thus, the human T-cell population of the present invention can be used as a material for researches directed to reveal immunological mechanism. Since the human T-cell population of the present invention has an immunosuppressive activity, it can be prepared into pharmaceutical compositions directed to relieve diseases which can be treated by inducing immunotolerance, for example, autoimmune diseases such as rheumatism, diabetic type I, and Crohn's disease; allergic diseases such as food allergy, pollenosis, and atopic dermatitis; rejection reaction and graft-versus-host reaction induced when in transplantation; or it can be prepared into pharmaceutical compositions directed to treat various types of cancers and virus diseases via the action of cytotoxic activity. The content of the human T-cell population and the administration dose of the above-identified pharmaceutical compositions can be appropriately determined by considering the types and symptoms of diseases to be applied, as well as their administration routes and dosage forms. The human T-cell population of the present invention can be used in combination with a medicament (s) for treating the above-identified diseases, selected from physiologically active substances such as cytokines, chemokines, hormones or the like; antibodies; immunosuppressants; anticancer drugs; and anti-allergic agents or the like; or it can be used in combination with a substance(s) capable of improving the action and effect of the human T-cell population of the present invention.

In preparing the pharmaceutical compositions containing the human T-cell population of the present invention, a desired dosage form can be selected depending on their therapeutic purposes, administration routes, or the like. It is desirable that the human T-cell population contained in the pharmaceutical compositions should be administered alive and the human T-cell population is usually used intact after being suspended in a liquid or embedded with a gel along with an appropriate additive, or optionally encapsulated in an appropriate microcapsule or liposome before parenterally administered through injection or the like. It can be also used in such a manner of freezing to preserve the human T-cell population suspended in a medium or physiological saline containing dimethylsulfoxide or glycerine, and thawing the freezed product prior to use.

The following explain the present invention in detail:

EXAMPLE 1

Preparation of Human T-cell Population from Cord Blood

Blood specimens were collected from umbilical cords, which had been resected, when in delivery, from seven pregnant women (U1 to U7) who had received informed consent, and each specimen was diluted with RPMI1640 medium by about two times by volume, and in usual manner overlaid on FICOLL-HYPAQUE, and centrifuged to collect a layer containing mononuclear cells, followed by washing it with physiological saline to collect the mononuclear cells. "CD34 ISOLATION KIT", commercialized by Miltenyi Biotec Inc., CA, USA, was applied to the above mononuclear cells to remove CD34 positive mononuclear cells and to collect CD34 negative mononuclear cells. The resulting CD34 negative mononuclear cells were suspended in RPMI1640 medium supplemented with 10% (v/v) fetal calf serum and inoculated at a cell number of $3\times10^6$ cells per well to commercialized 6-well microplates, which ST2 cells (RCB0224 available from RIKEN BioResource Center, Tsukuba, Japan), a mouse stroma cell line, had been cultured and adhered to the base of each well at a cell number of $1\times10^6$ to $2\times10^6$ cells per well. After one to two weeks culture, the suspending cells were collected along with the culture media, transferred to 6-well microplates to which fresh stroma cells had been adhered and further cultured. These sequential procedures were repeated several times to culture for at least three weeks to generate proliferable blast cells exhibiting a homogeneous lymphocytic form, and further cultured for one to two weeks by a similar method as in the above, followed by, to purify the blasted cells, collecting cells accumulated near the boundary between a FICOLL layer and a culture liquid layer formed by FICOLL-HYPAQUE in usual manner to obtain human T cell populations U1 to U7.

EXAMPLE 2

Analysis of Cell Membrane Antigen

By flow cytometry analysis using an antibody against a cell membrane antigen relating to human lymphocyte, the human T cell populations obtained in Example 1 were analyzed. The testing cells (U1 to U7) were treated for 30 min with antibodies against the antigens as listed in the following Table 1; a mouse anti-CD3 antibody (commercialized by Nichirei Biosciences Inc., Tokyo, Japan), mouse anti-CD4 antibody (commercialized by Nichirei Biosciences Inc., Tokyo, Japan), mouse anti-CD8α antibody (produced by Bechman Coulter K.K., Tokyo, Japan), mouse anti-CD25 antibody (produced by Bechman Coulter K.K., Tokyo, Japan), mouse anti-CD45RA antibody (produced by Bechman Coulter K.K., Tokyo, Japan), mouse anti-CD45RO antibody (commercialized by Nichirei Bioscience Inc., Tokyo, Japan), mouse anti-CD28 antibody (commercialized by Nichirei Bioscience Inc., Tokyo, Japan), mouse anti-CD56 antibody (produced by Bechman Coulter K.K., Tokyo, Japan), mouse anti-HLA-DR antibody (commercialized by Nichirei Bioscience Inc., Tokyo, Japan), mouse anti-TCRαβ antibody (produced by Japan Becton, Dickinson and Company, Tokyo, Japan), mouse antibody against glucocorticoid inducible tumor necrosis factor receptor (GITR) antibody (produced by R & D Systems Inc., MN, USA), mouse anti-CD152 antibody (produced by Bechman Coulter K.K., Tokyo, Japan), mouse anti-CD16 antibody (produced by Japan Becton, Dickinson and Company, Tokyo, Japan), mouse anti-CD57 antibody (produced by Japan Becton, Dickinson and Company, Tokyo, Japan), or as a negative control MOPC-21 mouse myeloma IgG antibody (produced by ICN Corporation, Niigata, Japan), and in usual manner further treated with fluorescein isothiocyanate (FITC) or a secondary antibody (goat anti-mouse IgG) bound with phycoerythrin (PE) for 30 min. The testing cells were analyzed on "EPICS XL", a product name of flowcytometer, produced by Bechman Coulter K.K., Tokyo, Japan. The results are in Table 1. In the table, "MFI", "%" and "–" show a mean value for fluorescent strength, positive percentage (percentage of the number of cells which exhibited a fluorescent strength of at least a threshold level provided based on that of the negative control), and not tested, respectively.

TABLE 1

| Cell membrane antigen | U1 % | U1 MFI | U2 % | U2 MFI | U3 % | U3 MFI | U4 % | U4 MFI | U5 % | U5 MFI | U6 % | U6 MFI | U7 % | U7 MFI |
|---|---|---|---|---|---|---|---|---|---|---|---|---|---|---|
| CD3 | 100 | 46 | 100 | 43 | 100 | 39 | 100 | 41 | 100 | 42 | 100 | 16 | 100 | 20 |
| CD4 | 67 | 3.2 | 66 | 4.5 | 80 | 9 | 88 | 16 | 80 | 16 | 65 | 5.7 | 91 | 21 |
| CD8α | 99 | 69 | 99 | 95 | 64 | 8.1 | 84 | 7.1 | 92 | 32 | 94 | 29 | 72 | 6 |
| CD25 | 99 | 9.5 | 93 | 13 | 94 | 19 | 97 | 6.7 | 99 | 94 | 98 | 21 | 93 | 23 |
| CD45RA | 69 | 1.4 | 14 | 0.5 | 61 | 2 | — | — | — | — | — | — | — | — |
| CD45RO | 81 | 1.5 | 42 | 1.3 | 61 | 1.5 | — | — | — | — | — | — | — | — |
| CD28 | 99 | 8.4 | 75 | 6.1 | 94 | 6.2 | 99 | 7.4 | 96 | 13 | 89 | 5.1 | 95 | 6.3 |
| CD56 | 1.1 | 0.2 | 2.5 | 0.3 | 3.5 | 0.3 | — | — | — | — | — | — | — | — |
| HLA-DR | 92 | 7.5 | 85 | 9.8 | 84 | 7.2 | 59 | 1.7 | 94 | 36 | 63 | 2.3 | 80 | 9.1 |
| TCRαβ | 100 | 13 | 99 | 16 | 99 | 12 | — | — | — | — | — | — | — | — |
| GITR | — | — | — | — | — | — | 76 | 1.8 | 72 | 5.3 | 47 | 1.4 | 80 | 4.3 |
| CD152 (CTLA-4) | — | — | 1.2 | 0.3 | 0.4 | 0.3 | 0.8 | 0.2 | 1.7 | 0.5 | 3.2 | 0.4 | 2.8 | 0.4 |
| CD16 | 1.2 | 0.2 | 0.7 | 0.3 | 1.2 | 0.3 | — | — | — | — | — | — | — | — |
| CD57 | 1.8 | 0.2 | 0.7 | 0.3 | 0.8 | 0.3 | — | — | — | — | — | — | — | — |

As evident from the results in Table 1, the cell populations thus obtained exhibit positive percentages (%) of about 97 to 100 for CD3 and TCRαβ, meaning that they are cell populations consisting essentially of T cells, and most of the T cells are judged to have been activated because they exhibit positive percentages (%) of about 93 to 99 for CD25, about 75 to 99 for CD28, and about 59 to 94 for HLA-DR. It can be judged that there exists no conventionally known natural T cells in the human T cell populations of the present invention because they only exhibit positive percentages (%) of 0.7 to 1.2, about 1.1 to 3.5, and about 0.7 to 1.8 for D16, CD56, and CD57, respectively, which are the cell membrane antigens characteristic to natural killer T cells. The human T cell populations show positive percentages (%) of about 47 to 80 for GITR and have regulatory T cell-like characteristics. Although the human T cell populations gave a substantially negative result for CD152 (CTLA-4), the intracellular expression thereof was confirmed (not shown in the table).

EXAMPLE 3

Double Staining Analysis Using Anti-CD4 Antibody and Anti-CD8 Antibody

Figure 1:
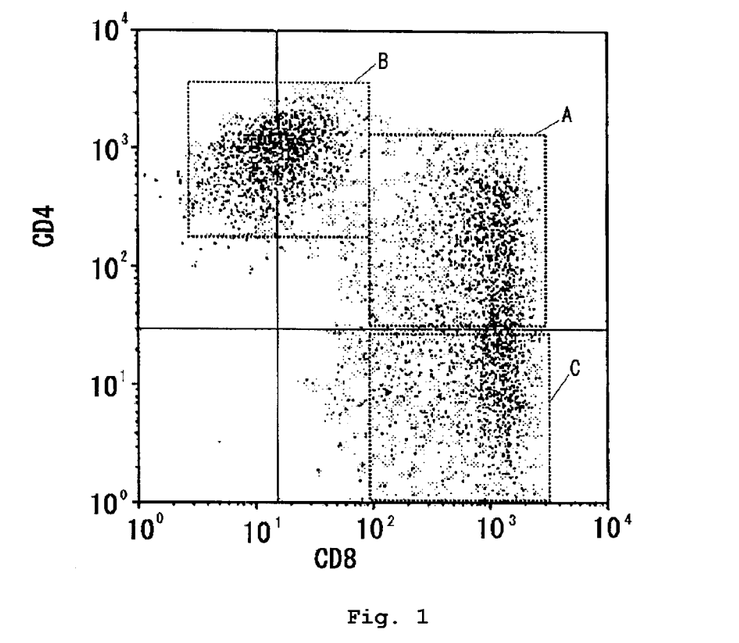
FIG. 1 is a figure of flow cytometry for expression distribution of CD4 and CD8 of the human T-cell population U3 according to the present invention.

According to usual manner, the seven human T cell populations (U1 to U7) obtained in Example 1 were double stained using a phycoerythrin-labeled mouse anti-CD4 antibody and a fluorescein isothiocyanate-labelled mouse anti-CD8 antibody (produced by Japan Becton, Dickinson and Company, Tokyo, Japan) and analyzed for flow cytometry by the method similarly as in Example 2. The human T cell populations U1, U2, U3 and U5 were re-analyzed one to two weeks after the first measurement. The results are in Table 2. The data in the upper and lower columns are respectively those for the first and second measurements. As representative examples, FIG. 1 is a figure of flow cytometry for human T-cell population U3 (first measurement).

TABLE 2

| Human T cell population | Group A (CD4$^+$CD8$^+$) (%) | Group B (CD4$^+$CD8$^{dim}$) (%) | Group C (CD4$^-$CD8$^+$) (%) | Total (%) |
|---|---|---|---|---|
| U1 | 27.1 | 13.4 | 59.2 | 99.7 |
|  | 30.6 | 32.2 | 36.0 | 98.8 |
| U2 | 45.0 | 15.8 | 36.8 | 97.6 |
|  | 43.7 | 24.0 | 31.0 | 98.7 |
| U3 | 25.5 | 49.2 | 23.8 | 98.5 |
|  | 51.6 | 1.1 | 43.6 | 96.3 |

TABLE 2-continued

| Human T cell population | Group A (CD4$^+$CD8$^+$) (%) | Group B (CD4$^+$CD8$^{dim}$) (%) | Group C (CD4$^-$CD8$^+$) (%) | Total (%) |
|---|---|---|---|---|
| U4 | 7.9 | 68.0 | 23.3 | 99.2 |
| U5 | 21.3 | 45.4 | 32.4 | 99.1 |
|  | 23.7 | 31.8 | 42.3 | 97.8 |
| U6 | 26.5 | 36.5 | 34.7 | 97.7 |
| U7 | 14.5 | 71.7 | 11.8 | 98.0 |

As shown in the results of Table 2, the tested human T cell populations contained a CD4$^+$CD8$^+$ group (Group A) at a percentage (%) of 7.9 to 51.6, a CD4CD8$^{dim}$ group (Group B) at a percentage (%) of 1.1 to 71.7, and a CD4$^-$CD8$^+$ group (Group C) at a percentage (%) of 11.8 to 59.2, reaching 96% or more in total. It was revealed that almost no cells with CD4$^-$CD8$^-$ exist. It was also found that, even the same human T cell population, it showed a phenomenon of a slight change in the ratio of the above three groups when cultured for one to two weeks.

EXAMPLE 4

Cytotoxic Activity Against Mouse Stroma Cells

According to conventional manner, as target cells, any of normal mouse fetal stroma cells collected from a fetal tissue of a CD-1 mouse with embryonic age of 13 to 16 days; commercialized cells of ST2 (RCB0224, available form RIKEN BioResource Center, Tsukuba, Japan), a mouse stroma cell line; OP9 (RCB1124, available from RIKEN BioResource Center, Tsukuba, Japan); and MC3T3-G2/PA6 (RCB1127, available from RIKEN BioResource Center, Tsukuba, Japan) were respectively inoculated to each well of 48-well microplates at a cell number of 4×10$^4$ cells, cultured overnight, inoculated with 4×10$^4$ cells (E/T ratio of 1/1), 8×10$^4$ cells (E/T ratio of 2/1), or 1.6×10$^5$ cells (E/T ratio of 4/1) of the human T-cell population U3, as effector cells, obtained in Example 1, and cocultured for 24 hours in RPMI1640 medium supplemented with 10% (v/v) fetal calf serum containing 100 U/ml of IL-2 to obtain testing wells. The culture supernatant was removed from each testing well, and the wells were washed twice with a fresh preparation of the same medium as described above to remove both the human T-cell population and detached dead-stroma cells in each well. To each well was added 0.4 ml of a fresh preparation of the same medium as described above and 30 μl of "ALAMAR BLUE", commercialized by Wako Pure Chemical Industries Ltd., Tokyo, Japan, followed by culturing for 18 hours. Metabolic activity was measured on fluorescence plate reader at an excitation wavelength of 544 nm and a detection wavelength of 590 nm after transferring 0.2 ml of the culture supernatant in each well to a 96-well flat base microplate. As a control well, there was provided a well similarly treated as above except for culturing only the above respective kinds of stroma cells as target cells. Cytotoxic activity was calculated based on the following Equation 1. The results are in Table 3.

Formula 1

$$\text{Cytotoxic activity (\%)} = \{1 - (\text{Measured value for testing well})/(\text{Measured value for control well})\} \times 100 \quad \text{Equation 1}$$

TABLE 3

| | Cytotoxic activity (%) | | |
|---|---|---|---|
| Target cell | E/T ratio = 1/1 | E/T ratio = 2/1 | E/T ratio = 4/1 |
| ST2 Cells | 97 | 100 | 99 |
| Normal mouse fetal stroma cells | 8 | 21 | 78 |
| OP9 Cells | 8 | 18 | 68 |
| MC3T3-G2/PA6 Cells | 14 | 10 | 63 |

As evident from the results in Table 3, the human T-cell population exerted a cytotoxic activity against ST2 cells at an E/T ratio of 1/1 and also exerted such a cytotoxic activity against mouse stroma cells other than the cells at an E/T ratio of 4/1. This result shows that the human T-cell population exerts a strong cytotoxic activity against mouse stroma cells used for coculturing to prepare it and also exerts a cytotoxic activity against another mouse stroma cells other than those used in coculturing, indicating that the human T-cell population has a cytotoxic activity with a relatively low cell-specificity.

EXAMPLE 5

Cytotoxic Activity Against other Cells

To examine whether the human T-cell population of the present invention exerts any cytotoxic activity against cells other than mouse stroma cells, the following experiment was conducted. Any one of the following cells as target cells was suspended in RPMI1640 medium supplemented with 10% (v/v) fetal calf serum and inoculated to 96-well flat base microplates at a cell number of $4 \times 10^4$ cells/well: MBT-2 cells, a mouse bladder cancer cell (RCB0544, RIKEN BioResource Center, Tsukuba, Japan); B16 cells, a mouse melanoma cell (RCB1283, RIKEN BioResource Center, Tsukuba, Japan); NHDF cells, a normal human skin fibroblastoid cell (commercialized by Kurashiki Spinning Co., Ltd., Okayama, Japan); HeLa cells, a human cervical carcinoma (RCB0007, RIKEN BioResource Center, Tsukuba, Japan); A431 cells, a human epidermoid carcinoma (RCB0202, RIKEN BioResource Center, Tsukuba, Japan); G361 cells, a human skin malignant melanoma (ATCC CRL-1424); and WiDr cells, a human colon cancer (JRCB0224, Health Science Research Resources Bank). According to a similar method as used in Example 4, the human T-cell population U3 obtained in Example 1 was inoculated to each of the above target cells at an E/T ratio ranging from 1/1 to 4/1, followed by measurement for cytotoxic activity by a similar method as used in Example 4. The results are in Table 4.

TABLE 4

| | Cytotoxic activity (%) | | |
|---|---|---|---|
| Target cell | E/T ratio = 1/1 | E/T ratio = 2/1 | E/T ratio = 4/1 |
| MBT-2 Cells (Mouse cancer cell) | 6 | 10 | 40 |
| B16 (Mouse cancer cell) | 7 | 8 | 11 |
| NHDF Cells (Human normal cell) | 2 | 2 | 3 |
| HeLa Cells (Human cancer cell) | 4 | 6 | 8 |
| A431 Cells (Human cancer cell) | 0 | 2 | 22 |
| G361 Cells (Human cancer cell) | 14 | 17 | 33 |
| WiDr Cells (Human cancer cell) | 0 | 0 | 92 |

As evident from the results in Table 4, the human T-cell population exerted a cytotoxic activity of not higher than 17% against every target cells at an E/T ratio of 2/1, however, it exerted a cytotoxic activity of ranging from 22 to 92% against MBT-2 cells, a mouse cancer cell line; WiDr cells, a human cancer cells; G361 cells; and A431 cells at an E/T ratio of 4/1. While the human T-cell population of the present invention only exerted a cytotoxic activity of 11% or lower against B16 cells, a mouse cancer cell; HeLa cells, a human cancer cell; and NHDF cells, a normal human cell at an E/T ratio of 4/1. The results in Examples 4 and 5 revealed that the human T-cell population of the present invention has a cytotoxic activity with a relatively low cell-specificity.

EXAMPLE 6

Grouping Based on Indexes of CD4 and CD8

To study the difference between the human T-cell population and conventionally known CD4$^+$CD25$^+$T$_{reg}$ or CD8$^+$ cytotoxic T cells, the human T-cell population was subjected to grouping by cell sorting based on indexes of CD4 and CD8. The human T-cell population U3, obtained in Example 1, was proliferated by coculturing with ST2 cells in the presence of IL-2 for two weeks, purified on FICOLL-HYPAQUE in usual manner, and suspended in a phosphate buffered saline (pH 7.4) containing 2 mM ethylenediamine tetraacetate and 0.5% (w/v) of calf serum albumin at a cell concentration of $6.7 \times 10^7$ cells/ml. According to usual manner, equal amounts of an anti-CD4 antibody labelled with phycoerythrin and an anti-CD8 antibody labelled with fluorescein isothiocyanate were added to the above cell suspension in an excessive amount to the cells, and the mixture was allowed to stand under ice-cold conditions for 30 min. To the resulting mixture was added 20-times volume of a fresh preparation of the same phosphate buffered saline, followed by removing excessive amounts of antibodies by centrifugation and further adding a fresh preparation of the same phosphate buffer as used in the above to the resultant to give a cell suspension with a cell density of $2.0 \times 10^7$ cells/ml. From the cell suspension, $7.4 \times 10^7$ cells were separated in usual manner using "FACSAria", a cell sorter produced by Japan Becton, Dickinson and Company, Tokyo, Japan, to separatory collect $0.7 \times 10^7$ cells (purity, 97.9%) of Group A with CD4$^+$CD8$^+$, $1.1 \times 10^7$ cells (purity, 99.4%) of Group B with CD4$^+$CD8$^{dim}$, and $1.9 \times 10^7$ cells (purity, 99.6%) of Group C, respectively. CD4⁻CD8⁻ cells could not be collected separatory because of their extremely low percentage.

EXAMPLE 7

Cytotoxic Activity for Groups

Similarly as in Example 4 except for using ST2 cells as target cells, the human T-cell population U3 obtained in Example 1 and the three groups obtained in Example 6 were used as effector cells and determined for their cytotoxic activities (%). The results are in Table 5.

TABLE 5

|  | Cytotoxic activity (%) | | |
|---|---|---|---|
|  | E/T ratio = 0.5/1 | E/T ratio = 1/1 | E/T ratio = 2/1 |
| Human T cell population U3 | 35.4 ± 7.9 | 64.5 ± 9.2 | 84.7 ± 5.9 |
| Group A (CD4⁺CD8⁺) | 55.0 ± 8.0 | 81.1 ± 1.0 | 84.2 ± 1.0 |
| Group B (CD4⁺CD8$^{dim}$) | 29.3 ± 7.3 | 43.2 ± 11.7 | 69.2 ± 3.0 |
| Group C (CD4⁻CD8⁺) | 63.6 ± 1.6 | 81.8 ± 1.0 | 82.1 ± 1.3 |

As evident from the results in Table 5, every group exerted a cytotoxic activity against ST2 cells. Particularly, Groups A and C gave a higher cytotoxic activity and Group B gave a rather lower level of such activity. In general, cytotoxic activity is recognized as a characteristic feature of CD4⁻CD8⁺ T cells, and the results show that not all the cytotoxic activity of the human T-cell population of the present invention is exerted by CD4⁻CD8⁺ T cells including CD8⁺ cytotoxic T cells.

EXAMPLE 8

Measurement for Immunosuppressive Activity

The human T-cell population U3 obtained in Example 1 and the three groups separatory collected in Example 6 were measured for their immunosuppressive activities by conventional autologous mixed-lymphocyte reaction.

As responsive cells, CD4⁺CD25⁻T cells were collected by the following method: Using conventional FICOLL-HY-PAQUE method, mononuclear cells were collected from human peripheral blood and applied to magnetic microbeads, to which an anti-CD25⁻ monoclonal antibody was bound, commercialized by Miltenyi Biotec Inc, CA, USA, to remove CD25⁺ cells and to obtain CD25⁻ cells. From the CD25⁻ cells, CD4⁺ cells were collected by applying magnetic micro-beads, to which an anti-CD4 monoclonal antibody had been bound, commercialized by Miltenyi Biotec Inc., CA, USA.

Dendritic cells as stimulating cells were collected as follows: By applying "MAGNETIC MICROBEADS", a product to which an anti-CD14 monoclonal antibody had been bound, commercialized by Miltenyi Biotec Inc., CA, USA, CD14⁺ mononuclear cells were collected from cord blood and cultured in the presence of granulocyte macrophage colony-stimulating factor (GM-CSF) and interleukin-4 (IL-4) for one to two weeks. Thereafter, dendritic cells were collected, cultured in the presence of lipopolysaccharide for two days, and treated in usual manner with mitomycin C just before being used in autologous mixed-lymphocyte reaction.

The above responsive cells and the stimulating cells were inoculated to each well of a microplate at respective cell numbers of 1×10⁵ cells and 5×10³ cells per well, and were inoculated with any of the human T-cell population U3 obtained in Example 1 and the three groups separatory collected in Example 6 at a cell number of 1×10⁵ cells per well, followed by culturing for seven days. At 16 hours before terminating the culture, an adequate amount of ³H-thymidine was added to the culture media in wells for use as testing wells. According to conventional manner, the uptake amount of ³H-thymidine was determined and calculated for immunosuppressive activity by the following Equation 2. As a control well, there was provided a well similarly treated as in the above except for not adding the human T cell population.

Formula 2:

$$\text{Immunosuppressive activity (\%)} = \{1-(\text{the uptake amount (cpm) of }^3\text{H-thymidine in testing well})/(\text{the uptake amount (cpm) of }^3\text{H-thymidine in control well})\} \times 100 \quad \text{Equation 2:}$$

TABLE 6

|  | Immunosuppressive activity (%) |
|---|---|
| Human T-cell population U3 | 99.6 |
| Group A (CD4⁺CD8⁺) | 99.6 |
| Group B (CD4⁺CD8$^{dim}$) | 99.5 |
| Group C (CD4⁻CD8⁺) | 99.6 |

As evident from the results in Table 6, all the human T-cell population and the three groups had immunosuppressive activities. The results indicate that both Group B with the same cell-membrane antigen as that of conventionally known CD4⁺CD25⁺T$_{reg}$ and Groups A and C with different cell-membrane antigen from CD4⁺CD25⁺T$_{reg}$ have immunosuppressive activities. Accordingly, this indicates that not all the immunosuppressive activity of the human T-cell population is exerted by CD4⁺CD8$^{dim}$ T cells including CD4⁺CD25⁺T$_{reg}$.

EXAMPLE 9

Expression Analysis of FOXP3

FOXP3, a transcription factor, is known as the one characteristically expressed in CD4⁺CD25⁺T$_{reg}$. The expression conditions of FOXP3 in the human T-cell population of the present invention and CD4⁺CD25⁺T$_{reg}$ were compared by the following experiment.

Preparation of CD4⁺CD25⁺T$_{reg}$

According to Godfrey et al., Blood, Vol. 105, pp. 750-758, 2005, CD4⁺CD25⁺T$_{reg}$ were prepared. CD34⁻ mononuclear cells derived from cord blood collected in Example 1 were suspended in RPMI1640 medium supplemented with 10% (v/v) fetal calf serum, placed in a microplate to which an anti-CD3/CD28 antibody had been adhered (wherein each well had been treated with 100 μl of 5 μg/ml of an anti-CD3 antibody and anti-CD28 antibody), and cultured for three days. An appropriate amount of 50 U/ml of IL-2 was further added to the culture, followed by culturing for one to two weeks and then analyzing the resulting culture on flow cytometry by double staining method using an anti-CD4⁺CD25⁺ antibody, revealing that about 95% of the cells were positive for CD4 and CD25. The cells thus obtained were subjected to the following test as a CD4⁺CD25⁺T specimen.

Expression Analysis of FOXP3 on RT-PCR

The expression levels of FOXP3 in both the CD4⁺CD25⁺T$_{reg}$ specimen prepared in the above and the human T-cell population U3 obtained in Example 1 were compared. Using "RNeasy Kit", produced by Qiagen K.K., Tokyo, Japan, total RNAs were respectively prepared from the above cells and used as templates to synthesize a first strand cDNA using a reverse transcriptase. Using as a template one nanogram of the obtained cDNA and an oligonucleotide primer having oligonucleotide sequences disclosed in SEQ ID NOs: 1 and 2, it was specifically amplified by conventional PCR. The resulting PCR product was in usual manner separated by agarose electrophoresis and treated by staining with ethidium bromide, followed by analyzing the bands for proliferated fragments (409 bp, 304 bp) specific to FOXP3. The results are in FIG. 2. FOXP3 contains two proteins with different splicings (Genbank NM_014009 and DQ010327), and in this example two bands of proliferated fragments with 409 bp and 304 bp will be expressed. As for $CD4^+CD25^+T_{reg}$, the data is also shown when the cells were cultured in a microplate to which an anti-CD3/CD28 antibody had been adhered.

Figure 2:
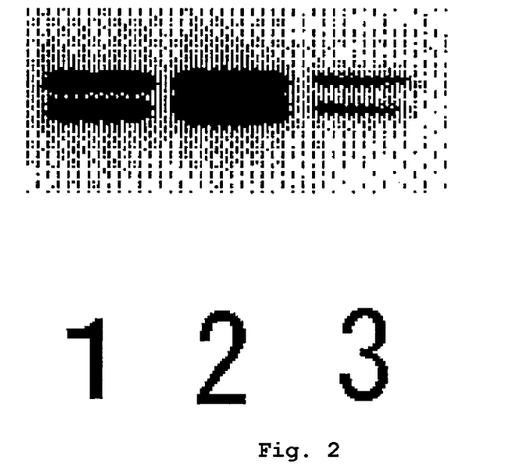
FIG. 2 is a figure of RT-PCR analytic result of FOXP3 for $CD4^+CD25^+$T cells and the human T-cell population U3 according to the present invention.

The expression levels of FOXP3 mRNA can be compared based on the shading of the band of each lane in FIG. 2. Lane "1" shows the expression level of FOXP3 mRNA in $CD4^+CD25^+T_{reg}$ and as disclosed in the above-identified literature of Godfrey et al., the expression level was more increased when treated with the anti-CD3/CD28 antibody (lane "2"). While the expression level of FOXP3 mRNA in the human T-cell population of the present invention (lane "3") was lower than that of $CD4^+CD25^+T_{reg}$ and, as the data is not shown, the human T-cell population did not substantially increase in its FOXP3 expression level even when treated with the anti-CD3/CD28 antibody. The results indicate that the human T-cell population of the present invention expresses FOXP3 similarly as in $CD4^+CD25^+T_{reg}$, however, the expression level is slightly lower.

Expression Analysis of FOXP3 on Western Blotting

From each of the human T-cell population U3 obtained in Example 1 and the three groups separatory collected in Example 6, equal numbers of cells were collected and treated with an aqueous solution containing 4.6% (w/v) of sodium dodecyl sulfate (SDS), 125 mM of Tris-HCl (pH 6.8), 20% (w/v) glycerine, and 1.4 M of β-mercaptoethanol to obtain a cell extract, followed by subjecting the cell extract to 10% SDS-polyacrylamide gel electrophoresis (SDS-PAGE) in usual manner. According to conventional manner, the resulting gel after electrophoresis was blotted onto a nitrocellulose membrane which was then treated with a goat anti-human FOXP3 antibody (produced by Abcam Inc., MA, USA) and further treated with a peroxidase-labelled anti-goat antibody (produced by Dako Inc., CA, USA) as a secondary antibody. The resulting nitrocellulose membrane after the antibody treatment was subjected to "SPERSIGNAL WEST PICO", a product name of chemiluminescent detection reagent kit produced by Pierce Chemical Company, IL, USA, followed by staining the bands of FOXP3 with luminol for chemiluminescence. The results are in FIG. 3.

Figure 3:
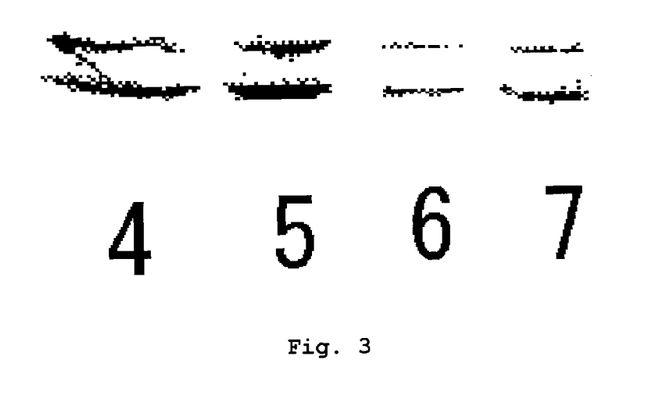
FIG. 3 is a figure of Western-blotting analytic result of FOXP3 for both the human T-cell population U3 according to the present invention and each group thereof.

In FIG. 3, Lanes "4", "5", "6" and "7" are respectively the results of Western blotting for the human T-cell population U3, Group A, Group B, and Group C. As evident from these results, FOXP3 was expressed not only in Group B which has the same cell membrane antigen as that of $CD4^+CD25^+T_{reg}$ but also expressed in Groups A and C which have different membrane antigens from that of $CD4^+CD25^+T_{reg}$. The results support the results in Example 8 and indicate that the immunosuppressive activity of the human T-cell population highly correlates with the expression of FOXP3 similarly as in $CD4^+CD25^+T_{reg}$ and also indicate that Groups A and C contain $CD4^+CD25^+T_{reg}$-like cells.

EXAMPLE 10

Proliferative Property Influenced by Cytokine or Mitogen

The human T-cell population of the present invention is not proliferative when cultured alone. The following experiment was conducted to examine the proliferative property of the human T-cell population when treated with an anti-CD3/CD28 antibody, cytokines, or mitogens. The human T-cell population U3 obtained in Example 1 and the $CD4^+CD25^+T_{reg}$ specimen prepared in Example 9 were respectively inoculated to the wells of a 96-well microplate at a cell number of $4 \times 10^4$ cells per well and incubated for five days after the addition of an anti-CD3/CD28 antibody, IL-2, IL-15, interleukin-4 (IL-4), interleukin-7 (IL-7), phytohemagglutinin (PHA), pokeweed mitogen (PWM), or concanavalin A (ConA) to each well. As a control well, there was provided a well where the human T-cell population was cultured alone. The $^3$H-thymidine uptake level in each well was assayed in usual manner. Cell proliferation was evaluated based on the level (cpm) of $^3$H-thymidine uptake in the control. The results are in Table 7.

TABLE 7

| | Cell proliferation activity (cpm) | |
|---|---|---|
| Treatment | Human T cell population (U3) | $CD4^+CD25^+T_{reg}$ |
| Untreated | 830 | 760 |
| Anti-CD3/CD28 antibody | 810 | 670 |
| Anti-CD3/CD28 antibody+ | | |
| IL-2 10 U/ml | 6,700 | 810 |
| IL-2 10 U/ml | 1,300 | 780 |
| IL-2 100 U/ml | 2,900 | 860 |
| IL-15 10 ng/ml | 2,600 | 810 |
| IL-15 100 ng/ml | 6,200 | 620 |
| IL-4 10 ng/ml | 520 | 560 |
| IL-7 10 ng/ml | 410 | 440 |
| Phytohemagglutinin (PHA) 5 µg/ml | 440 | 390 |
| Pokeweed mitogen (PWM) 5 µg/ml | 520 | 370 |
| Concanavalin A (ConA) 5 µg/ml | 370 | 490 |

As evident from the results in Table 7, the human T-cell population of the present invention did not proliferate when treated with the anti-CD3/CD28 antibody. This indicates that, similarly as in conventionally known regulatory T cells, the human T-cell population is deemed to be in the state of anergy or immunological unresponsiveness against antigen stimulation. Unlike conventionally known regulatory T cells, the human T cell population, however, proliferated when treated with IL-2 or IL-15 and exhibited a distinct proliferative activity when treated with the anti-CD3/CD28 antibody plus IL-2. The results indicate that the human T-cell population of the present invention is a cell population containing cells which have a different feature from those of conventional regulatory T cells. Further, the human T-cell population of the present invention is considered to have a different feature from those of conventional T cells because it does not proliferate even when treated with cytokines such as IL-4 and IL-7, as well as mitogens, which are growth factors for T cells.

EXAMPLE 11

Production of IL-10

The human T-cell population U3 according to the present invention obtained in Example 1 was prepared into a cell suspension with a cell density of $2 \times 10^5$ cells/ml, and 100

U/ml of IL-2 was added to the cell suspension, followed by inoculating one milliliter aliquots of the resulting cell suspension to the wells of a 24-well microplate or the wells of a 24-well microplate, to which an anti-CD3/CD28 antibody had been bound, and culturing the cells for 16 hours. The human T-cell population U3 was prepared into a cell suspension with a cell density of $3\times10^5$ cells/ml, and 100 U/ml of IL-2 was added to the cell suspension. Two milliliter aliquots of the resulting cell suspension were inoculated to a 6-well-microplate, whose well surfaces had been overlaid with ST2 cells that had been cultured up to a confluent state, and cultured for 40 hours. The resulting cultures were centrifuged to collect their culture supernatants which were then assayed for IL-10 concentration on an assay kit using an anti-IL-10 antibody (produced by eBioscience Inc., CA, USA). The results are in Table 8.

TABLE 8

| Culture conditions | IL-10 Production level (ng/ml) |
|---|---|
| Single culturing for 16 hours in the presence of IL-2 | 0.017 |
| Single culturing in anti-CD3/CD28 antibody bound well for 16 hours in the presence of IL-2 | 4.3 |
| Coculturing with ST2 cells for 40 hours in the presence of IL-2 | 4.6 |

As evident from the results in Table 8, the human T-cell population of the present invention produced IL-10 in the presence of IL-2 and distinctly increased in the IL-10 production level when cocultured with stroma cells. In the single culture system, the IL-10 production level of the human T-cell population was distinctly increased by the stimulation of the anti-CD3/CD28 antibody in the presence of IL-2. It is known that IL-10 is a cytokine that mainly plays a role of immunosuppression, and it is produced by type II helper T cells among T cells, and further it suppresses the production of cytokines such as interferon-$\gamma$ (IFN-$\gamma$) produced by type I helper T cells or the production of inflammatory cytokines such as IL-1 produced by macrophages. Thus, it can be estimated that the human T-cell population of the present invention exerts an immunosuppressive activity through the production of IL-10.

EXAMPLE 12

Obtention of Human T-cell Population from Peripheral Blood

Peripheral blood, collected from 18 healthy volunteers, was diluted with FCS-free RPMI1640 medium by 2-times and subjected to conventional FICOLL-HYPAQUE method to collect mononuclear cells. The collected mononuclear cells were prepared into a cell suspension with a cell concentration of $1\times10^6$ cells/ml by using a fresh preparation of the same medium as used in the above, and three milliliter aliquots of the cell suspension were inoculated to each well of a 6-well culture plate, where ST2 cells, a mouse stroma cell, had been cultured to a confluent state, followed by coculturing for four to five weeks similarly as in Example 1. The generated blast cells were purified by the FICOLL-HYPAQUE method and succeeded in obtaining human T cell populations P1 to P5 from peripheral blood from four healthy volunteers, where the human T cell populations P2 and P3 were the populations obtained from the same volunteer.

EXAMPLE 13

Analysis of Cell-membrane Antigen

By using a similar method as in Example 2, cell-membrane antigens for the human T cell populations P1 to P5 obtained in Example 12 were examined. The mouse anti-TCR$\gamma\delta$ antibody used was a product produced by T Cell Science, Inc., MA, USA. The results are in Table 9. The numerals in parentheses are the values measured after 9 to days of proliferation cultures of coculturing with ST2 cells in the presence of IL-2 (P3 was not cultured in the presence of IL-2), and the symbol "–" means "not measured".

TABLE 9

| Cell-membrane antigen | P1 (IL-2) | P2 (IL-2) | P3 | P4 (IL-2) | P5 (IL-2) |
|---|---|---|---|---|---|
| CD3 | 99.6 (99.5) | 99.8 (99.5) | 99.9 | 98.6 (99.9) | 99.9 (99.8) |
| CD4 | 91.1 (28.7) | — (—) | 48.3 | — (—) | — (—) |
| CD8$\alpha$ | 96.1 (97.8) | — (—) | 95.5 | — (—) | — (—) |
| CD25 | 98.0 (71.1) | 92.7 (82.6) | 91.2 | 77.7 (47.9) | 92.7 (51.9) |
| CD45RA | 46.0 (86.1) | 2.0 (13.5) | 33.9 | 12.1 (55.4) | 8.4 (21.7) |
| CD45RO | 64.0 (36.9) | 30.2 (14.5) | 11.8 | 1.0 (0.53) | 1.6 (3.3) |
| CD28 | 99.8 (99.5) | 98.1 (88.7) | 94.9 | 94.5 (76.5) | 98.4 (91.9) |
| CD56 | 1.6 (6.4) | 1.1 (3.1) | — | — (—) | — (—) |
| HLA-DR | 96.3 (99.4) | 61.1 (55.8) | 59.6 | 78.1 (62.7) | 88.3 (96.8) |
| TCR$\alpha\beta$ | 98.3 (86.1) | 99.2 (97.2) | 99.5 | 90.5 (93.6) | 99.2 (99.1) |
| TCR$\gamma\delta$ | 6.9 (23.0) | 0.8 (0.7) | 0.6 | 1.32 (2.68) | 0.8 (1.6) |
| GITR | 76.5 (54.2) | 64.0 (69.4) | 55.4 | — (—) | — (—) |
| CD152 (CTLA-4) | 1.3 (1.2) | — (—) | 0.9 | — (—) | — (—) |
| CD16 | 3.1 (1.0) | 5.4 (2.4) | — | — (—) | — (—) |
| CD57 | 1.3 (2.0) | 6.2 (6.6) | — | — (—) | — (—) |

As evident from the results in Table 9, the human T cell populations P1 to P5 according to the present invention have positive percentages of 90% or higher for CD3 and TCR$\alpha\delta$, indicating that they are cell populations consisting essentially of T cells; and the human T cell populations P1 to P5 have relatively high positive percentages for CD25, CD28, and HLA-DR, indicating that substantially most of the whole T cells contained therein would have been activated. The fact that CD16, CD56 and CD57, as characteristic cell-membrane antigens to natural killer T cells, were almost negative led to a conclusion that the human T cell populations P1 to P5 do not contain conventional natural killer cells. These human T cell populations had positive percentages of about 50% or higher for GITR and had regulatory T cell-like features. Although not shown in the table, the expression of intracellular CD152 (CTLA-4) was observed. From the results in the above and Table 2 in Example 2, it can be concluded that the human T cell populations obtained from peripheral blood and cord blood have similar characteristics in terms of cell-membrane antigens.

When continued culturing in the presence of IL-2, the human T-cell population obtained from peripheral blood tends to lower the positive percentage of CD25. It is known that CD25 is an IL-2 receptor and negatively regulated when IL-2 binds thereunto. The human T cell populations P1 and P4 tend to increase their positive percentages of TCRγδ when cultured in the presence of IL-2.

EXAMPLE 14

Double Staining Analysis Using Anti-Cd4 Antibody and Anti-Cd8 Antibody

Similarly as in Example 3, the human T cell populations P1 to P5 obtained in Example 12 were subjected to double staining.

The results are in Table 10. As for the human T cell populations and P4, they were expressed with data measured twice at different measurement days. The numerals in parentheses are the values measured after 9 to 14 days of proliferation cultures of coculturing with ST2 cells in the presence of IL-2 (P3 was not cultured in the presence of IL-2).

TABLE 10

| Human T cell population | Group A (CD4$^+$CD8$^+$) (%) | Group B (CD4$^+$CD8$^{dim}$) (%) | Group C (CD4$^-$CD8$^+$) (%) | Total (%) |
| --- | --- | --- | --- | --- |
| P1 | 13.2 | 46.1 | 36.7 | 96.0 |
| After two days | 10.3 | 37.6 | 45.6 | 93.5 |
| (IL-2) | (6.4) | (6.7) | (65.8) | (78.9) |
| P2 | 21.2 | 32.0 | 46.3 | 99.5 |
| (IL-2) | (29.1) | (20.0) | (49.6) | (98.7) |
| P3 | 19.0 | 26.7 | 51.8 | 97.5 |
| P4 | 11.5 | 30.3 | 54.6 | 96.4 |
| After four days | 11.1 | 15.3 | 71.9 | 98.3 |
| (IL-2) | (15.4) | (9.7) | (67.2) | (92.3) |
| P5 | 13.6 | 6.6 | 79.4 | 99.6 |
| (IL-2) | (10.6) | (1.1) | (87.4) | (99.1) |

Figure 4:
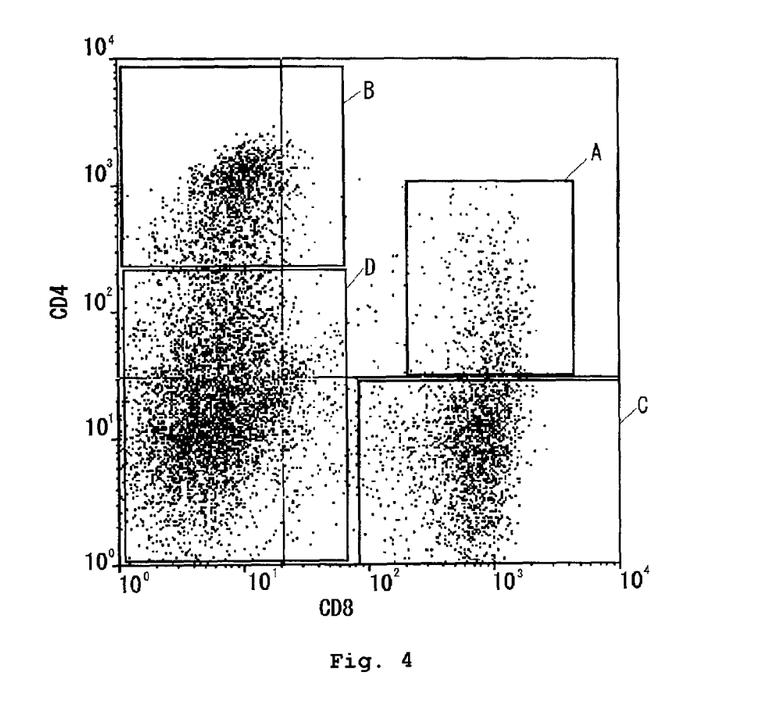
FIG. 4 is a figure of flow cytometry for expression distribution of CD4 and CD8 of the human T-cell population P1 according to the present invention.
Figure 5:
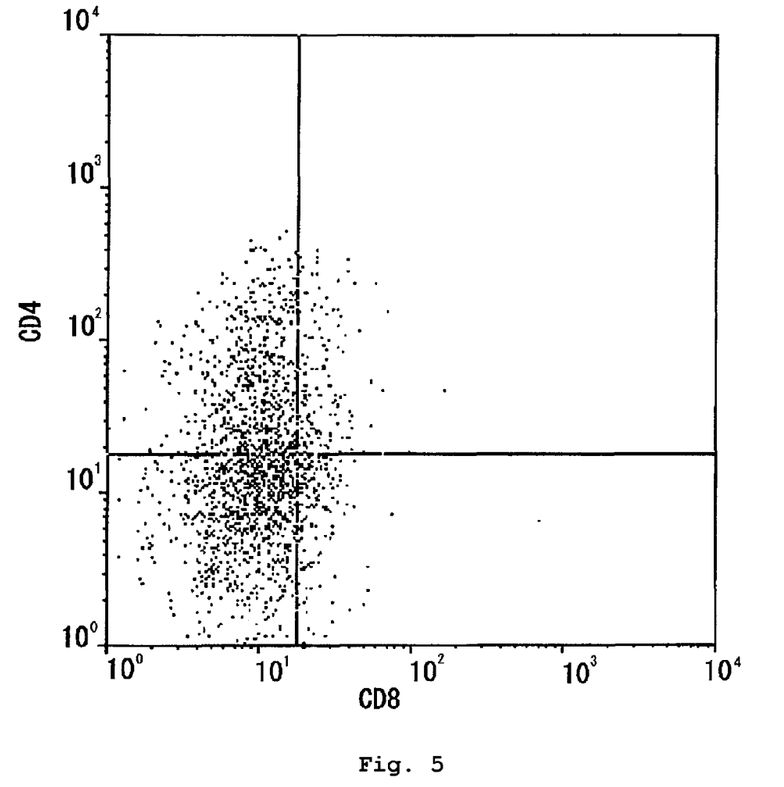
FIG. 5 is a figure of flow cytometry for expression distribution of TCRγδ of the human T-cell population P1 according to the present invention.

As shown in the results of Table 10, the tested human T cell populations P1 to P5 contained 10.3 to 21.2% of Group A, 6.6 to 46.1% of Group B, and 36.7 to 79.4% of Group C, which totaled to 93.5% or more. Unlike the human T-cell population obtained from cord blood, P1 and P4 contained a contaminated cell population with the expression of CD4$^{dim}$ CD8$^{dim}$, which tended to increase when cultured in the presence of IL-2. FIG. 4 is a flow cytometry for P1 as a typical example. The results in FIG. 5 depicting a flow cytometry by triple staining method for CD4, CD8 and TCRγδ revealed that the above CD4$^{dim}$ CD8$^{dim}$ cell population is a TCRγδ$^+$ cell population.

EXAMPLE 15

Cytotoxic Activity

Using "ANTI-TCRγ/δ MICROBEADS KIT", a product name of a kit commercialized by Miltenyi Biotec Inc., CA, USA, the cell population of Group D was removed from the human T-cell population P1 according to the present invention and examined, similarly as in Examples 4 and 5, whether P1 exerts a cytotoxic activity against mouse stroma cells, human normal cells, and human cancer cells at an E/T ratio of 4/1 or 8/1. The cell lines used were ST2 cells, NHDF cells, ZR-75-1 cells (derived from human breast cancer, RCB1906 available form RIKEN BioResource Center, Tsukuba, Japan), MKN45 cells (derived from human gastric cancer, RCB1001 available from RIKEN BioResource Center, Tsukuba, Japan), G361 cells, LoVo cells (derived from human colon cancer, RCB1639 available from RIKEN BioResource Center, Tsukuba, Japan), COLO 320DM cells (derived from human colon cancer, ATCCCCL-220), and WiDr cells. The results are in Table 11. In Table 11, the symbol "–" means "not measured".

TABLE 11

| | Cytotoxic activity (%) | |
| --- | --- | --- |
| Target cells | E/T ratio = 4/1 | E/T ratio = 8/1 |
| ST2 Cell (mouse stroma cell) | 88.1 ± 2.0 | 95.4 ± 1.1 |
| NHDF Cell (human normal cell) | 2.5 ± 2.2 | –0.6 ± 8.6 |
| ZR-75-1 Cell (human cancer cell) | — | 50.8 ± 15.8 |
| MKN45 Cell (human cancer cell) | — | 59.4 ± 6.5 |
| G361 Cell (human cancer cell) | 54.2 ± 13.8 | 86.8 ± 2.3 |
| LoVo Cell (human cancer cell) | — | 63.9 ± 22.4 |
| COLO 320DM Cell (human cancer cell) | — | 77.5 ± 15.5 |
| WiDr Cell (human cancer cell) | 51.3 ± 1.9 | 87.0 ± 7.3 |

As evident from the results in Table 11, the human T-cell population P1 showed a cytotoxic activity against mouse stroma cells and human cancer cells when used at an E/T ratio of 4/1 or 8/1, but it did not substantially show any cytotoxic activity against NHDF cell, a human normal cell, even when used at an E/T ratio of 8/1. From these results, it was revealed that, similarly as the human T-cell population obtained from cord blood, the human T-cell population obtained from peripheral blood exerts no cytotoxic activity against normal cells and has a cytotoxic activity with a lesser cell-specificity against cancer cells.

EXAMPLE 16

Cytotoxic Activity of Each Group, which had been Grouped Thereinto with an Index of CD4 and CD8

The human T-cell population P1 obtained in Example 12 was proliferated by coculturing with ST2 cells in the presence of IL-2 for two weeks and grouped similarly as in Example 6 into the following four groups after being separatory collected from 6.5×10$^7$ cells: 3.0×10$^6$ cells in Group A (purity 97.1%), 4.6×10$^6$ cells in Group B (purity 94.6%), 1.7×10$^7$ cells in Group C (purity 99.3%), and 3.0×10$^6$ cells in Group D (purity 91.2%). Similarly as in Example 7, these groups were determined for their cytotoxic activities (%). The results are in Table 12.

TABLE 12

| | Cytotoxic activity (%) | | |
| --- | --- | --- | --- |
| | E/T ratio = 0.5/1 | E/T ratio = 1/1 | E/T ratio = 2/1 |
| Human T cell population P1 | 67.0 ± 2.9 | 86.5 ± 0.9 | 90.2 ± 0.8 |
| Group A (CD4$^+$CD8$^+$) | 45.7 ± 4.4 | 68.2 ± 4.6 | 81.5 ± 4.6 |
| Group B (CD4$^+$CD8$^{dim}$) | 9.5 ± 17.3 | 37.3 ± 3.5 | 55.7 ± 1.7 |
| Group C (CD4$^-$CD8$^+$) | 57.4 ± 4.2 | 77.0 ± 0.3 | 86.7 ± 2.2 |
| Group D (CD4$^{dim}$CD8$^{dim}$) | 61.1 ± 5.0 | 86.3 ± 0.6 | 90.6 ± 1.2 |

As evident from the results in Table 12, the human T-cell population P1 and all the groups contained therein exerted cytotoxic activities against ST2 cells, particularly, Groups A and C had higher cytotoxic activities. The results can be said to be nearly the same results as in Table 5 in Example 7 for the human T-cell population obtained from cord blood. Since the cell population of Group D, as a characteristic feature of P1, obtained from peripheral blood had a stronger cytotoxic activity than those of other groups and had TCRγδ positiveness, it can be judged to be conventional cytotoxic T cells.

EXAMPLE 17

Measurement for Immunosuppressive Activity

Similarly as in Example 8, the human T-cell population P1 or the four groups separatory collected in Example 16 were measured for their immunosuppressive activities. The human T-cell population P1 was used after being proliferated by coculturing with ST2 cells in the presence of IL-2 for two weeks. The results are in Table 13.

TABLE 13

|  | Immunosuppressive activity (%) |
| --- | --- |
| Human T-cell population P1 | 68.8 |
| Group A ($CD4^+CD8^+$) | 76.4 |
| Group B ($CD4^+CD8^{dim}$) | 22.6 |
| Group C ($CD4^-CD8^+$) | 74.5 |
| Group D ($CD4^{dim}CD8^{dim}$) | 15.2 |

As evident from the results in Table 13, there was found a tendency that the human T-cell population P1 obtained from peripheral blood showed a slightly lower immunosuppressive activity than that of the human T-cell population obtained from cord blood, particularly, the cell population of Group B showed a tendency to lower immunosuppressive activity. It can be estimated that the cell population of Group B was susceptible to be damaged by cell sorting method for separating cells, resulting in its immunosuppressive activity. Considering this, the human T cell populations obtained from peripheral blood and cord blood, respectively, can be said to show substantially the same immunosuppressive activity. Group D, as a characteristic feature of P1, showed the lowest immunosuppressive activity among these groups and this coincided with the results in Example 16 which regard Group D as conventional cytotoxic T cells.

EXAMPLE 18

Proliferation by Cytokines or the Like

Similarly as in Example 10, the human T-cell population P1, collected from peripheral blood, was measured for $^3$H-thymidine uptake level (cpm) to evaluate whether the cell proliferation can be induced by a treatment with anti-CD3/CD28 antibody and/or cytokines. The human T-cell population P1 was used after proliferated by coculturing with ST2 cells in the presence of IL-2 for two weeks. The results are in Table 14.

TABLE 14

| Treatment | Cell proliferation activity (cpm) |
| --- | --- |
| Without treatment | 1,700 ± 830 |
| Anti-CD3/CD28 antibody | 4,200 ± 420 |
| Anti-CD3/CD28 antibody+ | |
| IL-2 10 U/ml | 4,100 ± 1,800 |
| IL-2 10 U/ml | 6,300 ± 420 |
| IL-2 100 U/ml | 2,600 ± 1,800 |
| IL-15 10 ng/ml | 7,400 ± 900 |
| IL-15 100 ng/ml | 6,700 ± 1,000 |
| IL-4 10 ng/ml | 4,100 ± 1,700 |
| IL-7 10 ng/ml | 6,000 ± 610 |

As evident from the results in Table 14, the human T-cell population P1 obtained from peripheral blood showed a distinct proliferation ability when treated with IL-2, IL-15 or a combination of an anti-CD3/CD28 antibody and IL-2, and showed a similar feature to that of the human T-cell population obtained from cord blood (cf. Table 7 in Example 10). Unlike the human T-cell population obtained from cord blood, the human T-cell population P1, which had been obtained from peripheral blood, proliferated when treated with the anti-CD3/CD28 antibody, revealing that it contained both cells not completely changed into the state of anergy and other cells which had been proliferated by IL-4 or IL-7 as a T cell growth factor.

EXAMPLE 19

Expression Analysis of FOXP3 by RT-PCR

Similarly as in Example 9, mRNAs were prepared from the human T cell populations P1 to P5 obtained from peripheral blood and examined for expression status of FOXP3 in terms of its mRNA level. The result revealed that the human T cell populations P1 to P5 expressed FOXP3, however, the expression level thereof was lower than that of the human T-cell population obtained from cord blood. The result would support the result that the human T-cell population obtained from peripheral blood has a lower immunosuppressive activity than that obtained from cord blood.

EXAMPLE 20

Production of IL-10

Similarly as in Example 11, the human T-cell population P1, obtained from peripheral blood, was subjected to measurement for IL-10 production level under different culture conditions. The human T-cell population P1 was used after proliferated by coculturing with ST2 cells in the presence of IL-2 for two weeks. The results are in Table 15.

TABLE 15

| Culture conditions | IL-10 Production level (ng/ml) |
| --- | --- |
| Single culture for 16 hours in the presence of IL-2 | 0.0034 |
| Single culture for 16 hours in well to which anti-CD3/CD28 antibody bound, in the presence of IL-2 | 2.4 |
| Coculture with ST2 cells for 40 hours in the presence of IL-2 | 1.0 |

As evident from the results in Table 15, the human T-cell population P1 produced IL-10 in the presence of IL-2 and the production level distinctly increased when cocultured with stroma cells. Even in the single culture system, the human T-cell population P1 distinctly increased in IL-10 production level when stimulated with the anti-CD3/CD28 antibody in the presence of IL-2. Comparing the results with those in Table 8 in Example 11, the human T-cell population collected from peripheral blood was revealed to be somewhat inferior to that obtained from cord blood in terms of IL-10 production ability.

Industrial Applicability

As described above, the human T-cell population of the present invention is a novel human T-cell population having both cytotoxic and immunosuppressive activities, and it can be useful in the treatment of autoimmune diseases and allergic diseases, as well as transplantation medical care, through the immunosuppressive activity; and also useful in cancer treatment through the cytotoxic activity.

The invention claimed is:

1. A human T-cell population obtainable by coculturing a mononuclear cell collected from human blood with a stroma cell, wherein:
  (a) the human blood is selected from the group consisting of cord blood and peripheral blood;
  (b) the human T-cell population contains cells that express CD3;
  (c) the human T-cell population contains cells that express CD25;
  (d) the human T-cell population contains cells that express CD28;
  (e) the human T-cell population contains cells that express T-cell antigen receptor αβ;
  (f) the human T-cell population contains subpopulations (i), (ii), and (iii), wherein
  subpopulation (i) is a CD4 positive and CD8 positive (CD4$^+$CD8$^+$) human T-cell group,
  subpopulation (ii) is a CD4 positive and CD8 dimly positive (CD4$^+$CD8$^{dim}$) human T-cell group, and
  subpopulation (iii) is a CD4 negative and CD8 positive (CD4$^-$CD8+) human T-cell group;
  (g) wherein at least 90% of the total cells in the human T-cell population are composed of subpopulation (i), subpopulation (ii), and subpopulation (iii);
  (h) the human T-cell population is free of human or mouse stroma cells; and
  (i) the human T-cell population produces interleukin-10 (IL-10).

2. The human T-cell population of claim 1, wherein
  7.9% to 51.6% of cells in the human T-cell population are subpopulation (i);
  1.1% to 71.1% of cells in the human T-cell population are subpopulation (ii); and
  11.8% to 79.4% of cells in the human T-cell population are subpopulation (iii);
  wherein the % is defined as the cell number of each of said groups (a) to (c) to the total number of cells in said human T-cell population.

3. A pharmaceutical composition comprising the human T-cell population of claim 1.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer for human FOXP3 mRNA (Genbank Code
   NM_014009 or DQ010327)

<400> SEQUENCE: 1
gcacccaaag cctcagacct                                            20

<210> SEQ ID NO 2
<211> LENGTH: 20
<212> TYPE: DNA
<213> ORGANISM: Artificial Sequence
<220> FEATURE:
<223> OTHER INFORMATION: PCR primer for human FOXP3 mRNA (Genbank Code
   NM_014009 or DQ010327)

<400> SEQUENCE: 2
gctccctgga cacccattcc                                            20